(12) United States Patent
Capanni et al.

(10) Patent No.: US 7,350,643 B2
(45) Date of Patent: Apr. 1, 2008

(54) SYSTEM AND DEVICE FOR KEEPING BONE SCREWS READY

(75) Inventors: Felix Capanni, Neu-Ulm (DE); Christian Knopfle, Donaueschingen (DE)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 431 days.

(21) Appl. No.: 10/758,908

(22) Filed: Jan. 16, 2004

(65) Prior Publication Data

US 2004/0173628 A1   Sep. 9, 2004

(51) Int. Cl.
B65D 83/10 (2006.01)
B65D 85/24 (2006.01)
A61B 17/58 (2006.01)

(52) U.S. Cl. .................... 206/370; 206/339; 606/73

(58) Field of Classification Search ................ 206/363, 206/370, 338–339, 343–347; 606/73, 96, 606/98, 100, 104, 72
See application file for complete search history.

(56) References Cited

U.S. PATENT DOCUMENTS

| | | | | |
|---|---|---|---|---|
| 3,211,284 A * | 10/1965 | Anstett | ................ | 206/346 |
| 3,718,252 A * | 2/1973 | Roeder | ................ | 206/343 |
| 4,955,476 A * | 9/1990 | Nakata et al. | ................ | 206/346 |
| 5,394,983 A * | 3/1995 | Latulippe et al. | ................ | 206/370 |
| 5,437,368 A * | 8/1995 | Mikels | ................ | 206/341 |
| 5,622,500 A | 4/1997 | Niznick | ................ | 433/173 |
| 5,732,821 A | 3/1998 | Stone et al. | ................ | 206/370 |
| 6,328,746 B1 * | 12/2001 | Gambale | ................ | 606/104 |
| 6,402,759 B1 * | 6/2002 | Strong et al. | ................ | 606/104 |
| 6,830,573 B2 * | 12/2004 | Strong et al. | ................ | 606/73 |
| 6,974,030 B1 * | 12/2005 | Sundstrom | ................ | 206/347 |
| 7,007,798 B2 * | 3/2006 | Happonen et al. | ................ | 206/370 |

FOREIGN PATENT DOCUMENTS

| | | |
|---|---|---|
| DE | 3601715 | 7/1987 |
| DE | 3807526 | 9/1989 |
| DE | 10025717 | 12/2002 |
| WO | WO0178619 | 10/2001 |

* cited by examiner

Primary Examiner—Bryon P. Gehman
(74) Attorney, Agent, or Firm—Howard & Howard Attorneys, P.C.

(57) ABSTRACT

A keeping-ready device for bone screws and a keeping-ready system comprising this keeping-ready device are described. The keeping-ready device has a surface, in which a plurality of orifices for accommodating the bone screws is provided. The keeping-ready device allows the bone screws to be kept ready countersunk in relation to the surface.

14 Claims, 6 Drawing Sheets

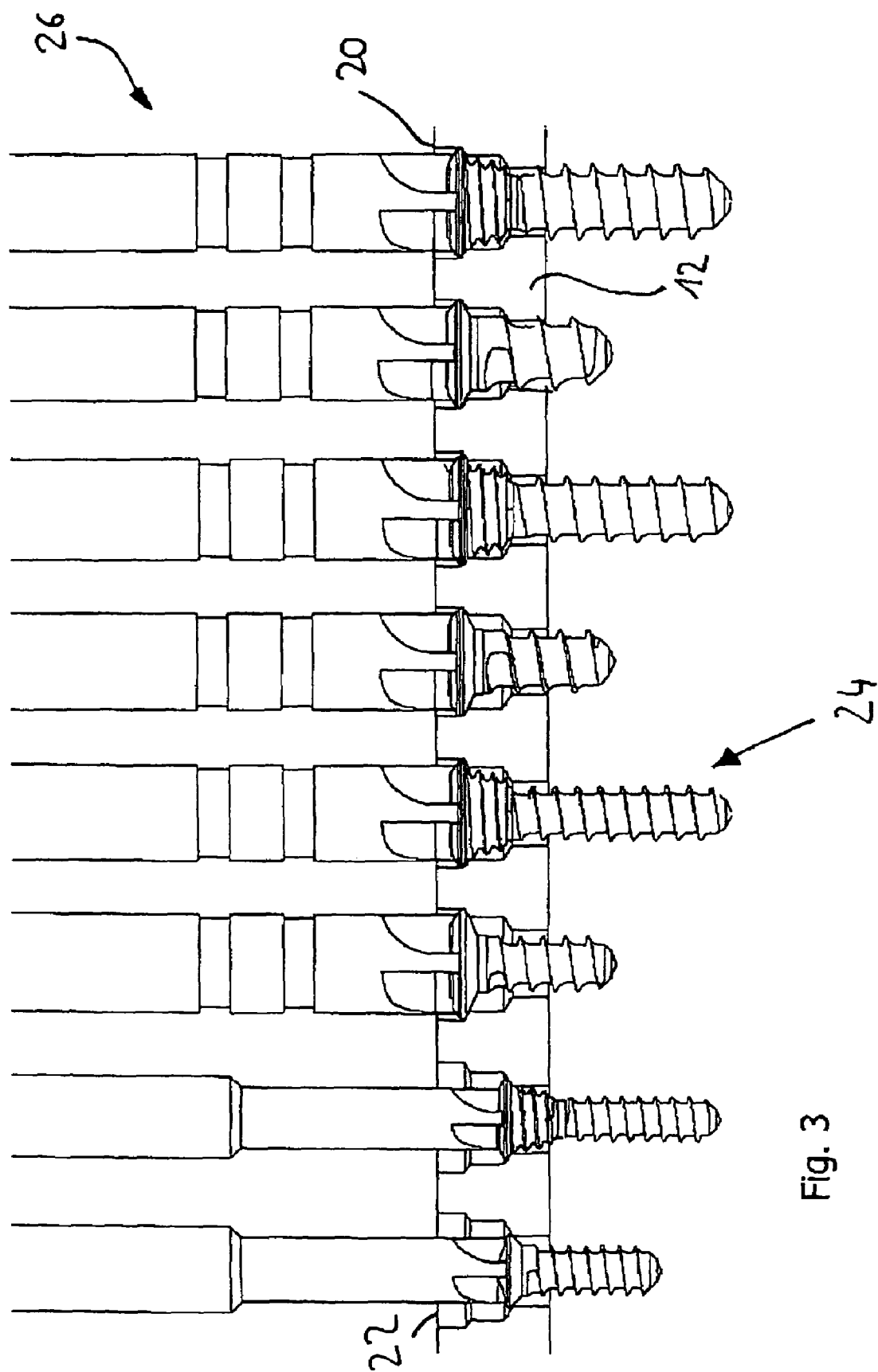

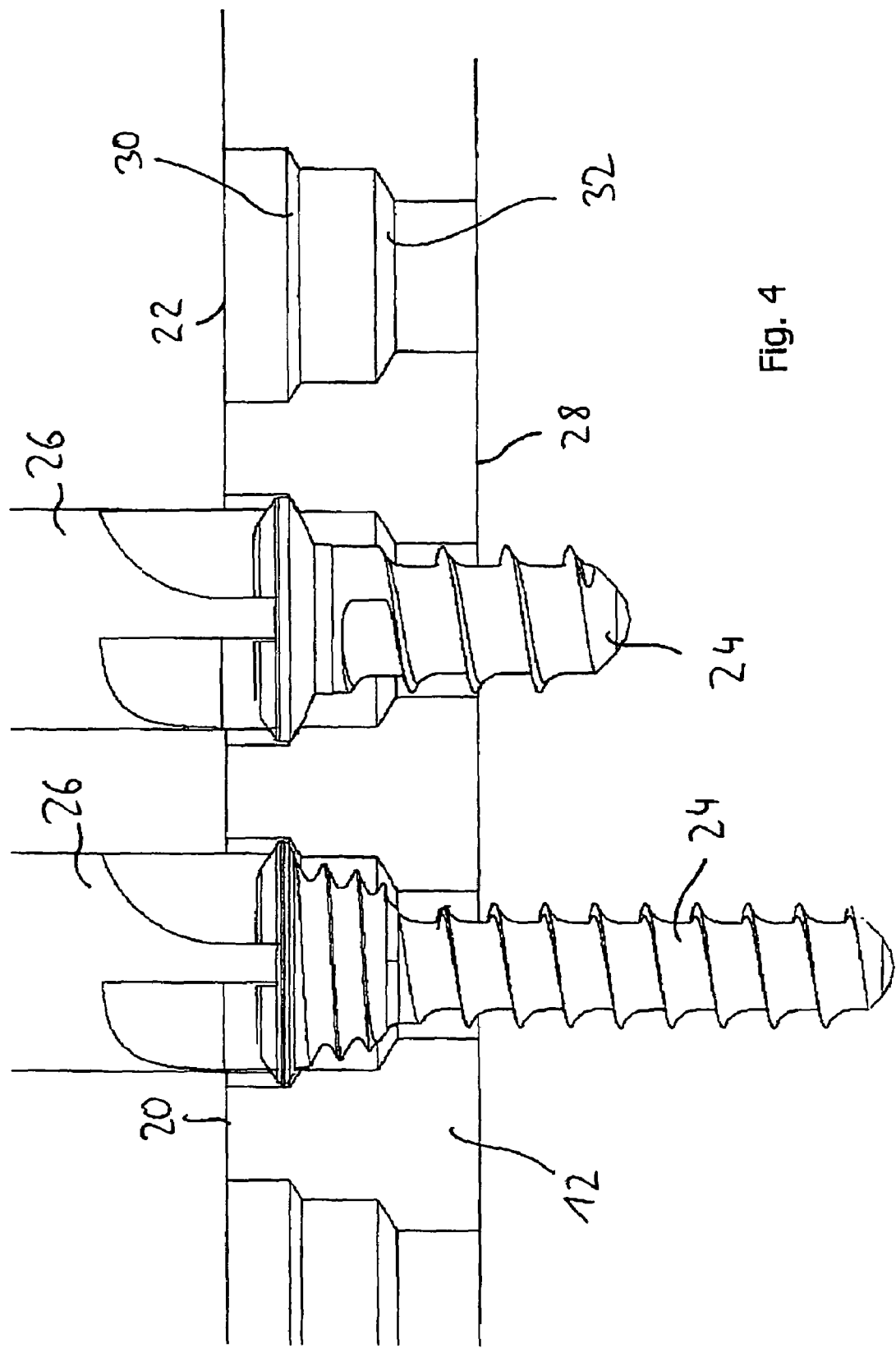

SYSTEM AND DEVICE FOR KEEPING BONE SCREWS READY

TECHNICAL FIELD

The invention relates to a device for keeping bone screws ready for a surgical operation. The invention further relates to a system for keeping bone screws ready, containing the keeping-ready device and a removal instrument for removing kept-ready bone screws from the keeping-ready device.

BACKGROUND OF THE INVENTION

Conventional keeping-ready devices for bone screws comprise a pick-up sheet provided with a multiplicity of orifices for inserting bone screws. The diameters of these orifices are chosen in such a way that on the one hand they are larger than the diameter of a screw shank, but on the other hand smaller than the diameter of a screw head. When a bone screw is inserted into one of the orifices, with an underside of the screw head facing the pick-up sheet the bone screw consequently comes into contact with the surface of the sheet.

Bone screws kept ready in this way are picked up from the sheet during a surgical operation by means of a suitable removal instrument, e.g. by a screw driver, and then screwed into a bone or into a fragment of a bone.

The use of conventional keeping-ready devices allows bone screws to be kept ready and picked up without their having to be taken into the hand. This is advantageous not only on grounds of hygiene, but also of ergonomics.

The object of the invention is to make available an improved keeping-ready device for bone screws and also a system comprising the improved keeping-ready device.

SUMMARY OF THE INVENTION

According to the invention, to achieve this object a system for keeping ready bone screws with a keeping-ready device for bone screws and also a removal instrument for removing a bone screw from the keeping-ready device and in particular for subsequently screwing the bone screw into a bone or into a fragment of a bone is proposed, wherein the keeping-ready device according to the invention has a surface with a plurality of orifices for inserting the bone screws and the keeping-ready device allows the inserted bone screws to be kept ready countersunk in relation to the surface. The removal instrument may be dimensioned in such a way that it can be inserted into the orifices for removal of the bone screws arranged as countersunk.

The removal instrument can be designed as a screw driver blade, which could allow for a self-holding pick-up of a bone screw. The self-holding pick-up can be produced, for example, by using magnetic or magnetised materials for the removal instrument or by providing means for a non-positive connection between the removal instrument on the one hand and the head of the bone screw on the other hand.

The dimensions of the removal instrument and the orifices may be matched to one another in such a way that, e.g. cylindrically designed delimitation walls of the orifices allow at least partial guiding of an insertion movement of the removal instrument. Guiding of this kind is produced in particular if the dimensions of the orifices are chosen as partially only minimally, preferably 2 to 20%, larger than the dimensions of the end of the removal instrument to be inserted into the orifices. However, it is also conceivable to choose the dimensions of the orifices as substantially larger.

As well as the already mentioned keeping-ready device and the removal instrument, the system for keeping ready bone screws according to the invention can comprise a plurality of bone screws, preferably with different head shapes. The bone screws can have a different shank diameter. Additionally the orifices of the keeping-ready device can be differently dimensioned.

As far as the orifices are concerned, there is the greatest variety of modes of implementation available. The orifice cross-section is preferably chosen as circular. Other orifice cross-sections (e.g. elliptical, square, etc.) can, however, also be provided. Advantageously the shape of the orifice cross-section is matched to the cross-section of the removal end of a removal instrument.

According to a first version of the invention the orifices are configured as pocket holes, which are preferably constructed in a keeping-ready device designed as a solid block. With orifices of pocket hole type the bone screws can be kept ready lying on the bottom of the pocket holes. The pocket holes can have different depths in order to pick up bone screws of different length.

According to a second version of the invention the orifices provided in a surface of the keeping-ready device are configured as through orifices. The through orifices can in this case be constructed in a thin (sheet) or thick first plate.

If the through orifices according to the second version of the invention are constructed in a first plate, there can be a second plate, e.g. parallel to the first plate. The second plate is preferably distanced from the first plate to such an extent that the bone screws are kept ready by the keeping-ready device, e.g. with their heads or tips lying on the second plate.

In practice it has proved with conventional keeping-ready devices that slipping of the removal instrument from the screw head leads to a kind of "trampoline effect" of the pick-up sheet and the screws can spring out of their orifices. To avoid this kind of trampoline effect the ratio of area to thickness of the first plate is preferably chosen in such a way that the first plate has no or only slight springing properties. The thickness of the first plate is preferably more than approximately 1 mm and in particular more than approximately 2 mm. Generally, said "trampoline effect" can be safely avoided at least if the delimitation walls of the orifices have an axial extension which guarantees an adequate guiding function for the removal instrument to be inserted into the orifices.

According to a preferred configuration of the invention delimitation walls of the orifices in a region below the surface have a reduction in inner diameter, which can act as a stop for a head of a bone screw to be kept ready. The reduction in inner diameter can have an inner diameter which decreases from the surface of the keeping-ready device at least partially constantly (e.g. conically) or in steps. The course of the decrease in inner diameter should be matched to the different head shapes of the usable bone screws.

The surface of the keeping-ready device advantageously has a multiplicity of more than 25 and in particular of more than 50 or 100 orifices. The orifices can be arranged in the surface like a grid. The ratio of the total area of the surface including the orifices to the total area of the orifices can be between 1.5:1 and 5:1 and preferably between 2:1 and 4:1.

SHORT DESCRIPTION OF THE DRAWINGS

Further advantages and configurations of the invention emerge from the following description of preferred embodiment examples and the figures.

FIG. 3 shows a cross-section through a plate-shaped element of the keeping-ready device according to FIGS. 1 and 2 in combination with a plurality of bone screws and removal instruments for the bone screws.

FIG. 4 shows an enlarged view of FIG. 3.

DESCRIPTION OF A PREFERRED EMBODIMENT

An embodiment of a system for keeping ready bone screws according to the invention is described below. The keeping-ready system according to the invention comprises in the example case different types of bone screws and removal instruments. The invention could also be used in combination with other bone screws or removal instruments.

Figure 1:
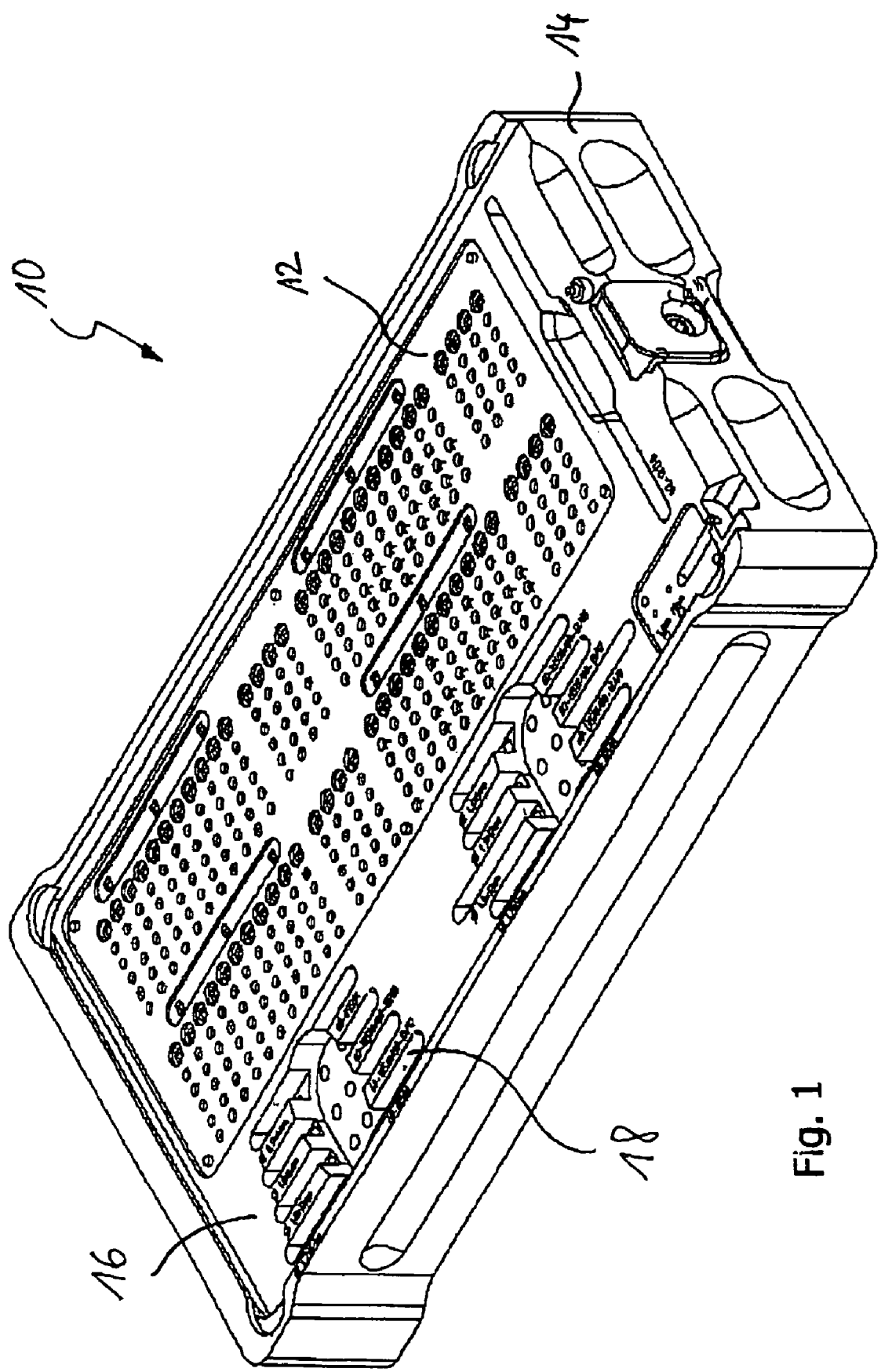
FIG. 1 shows a perspective view of a keeping-ready device according to the invention for bone screws, bone plates, etc.

In FIG. 1 a perspective view of a keeping-ready device 10 for bone screws according to the invention is illustrated in the empty state, i.e. without bone screws kept ready. The device 10 comprises a keeping-ready plate 12 and an accommodating frame 14 for the plate 12. By means of the frame 14 the plate 12 is positioned a few centimetres above a support plane (e.g. an operating table) of the frame 14. In addition to an accommodating area for the plate 12, a multiplicity of orifices 18 for accommodating bone plates, surgical instruments, such as screw drivers, etc., is constructed in a surface 16 of the frame 14. According to an alternative embodiment of the invention the device 10 is cut out of a single piece (e.g. a block of aluminium).

Figure 2:
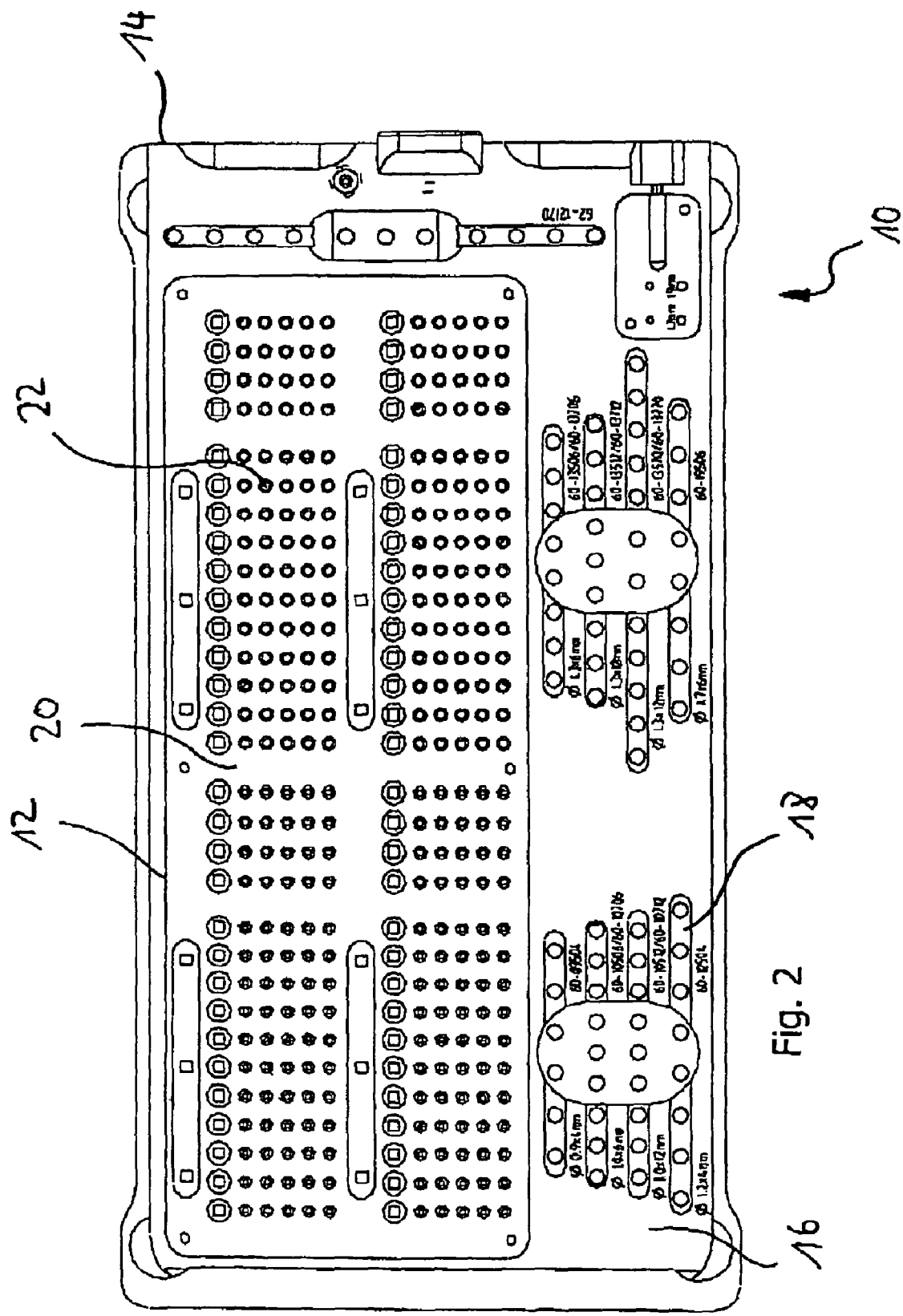
FIG. 2 shows an aspect on to the keeping-ready device according to FIG. 1.

FIG. 2 shows an aspect on to the keeping-ready device 10 according to FIG. 1. In FIG. 2 it can be clearly seen that the plate 12 has a surface 20 in which a multiplicity of orifices 22 is arranged like a grid. In the case illustrated in FIG. 2 the ratio of the total area of the surface 20 including the area of the orifices 22 to the total area of the orifices 22 is approximately 1:3.

FIG. 3 shows a section through the plate 12 according to FIG. 2 in the region of eight orifices 22 located next to one another. In the view according to FIG. 3 a plurality of different bone screws 24 which have been inserted into the orifices 22 is illustrated. Additionally, various removal instruments cooperating with the heads of the bone screws 24 are illustrated in the form of screw driver blades 26.

The heads of the bone screws are provided with a cross recessed structure in each case and the screw driver blades 26 likewise have a cross recessed structure in each case on their ends cooperating with the bone screws. The cross recessed structures of the heads of the bone screws 24 and the ends of the screw driver blades 26 are constructed in such a way that the ends of the screw driver blades 26 can be brought into non-positive locking engagement into the cross recessed structures of the heads of the bone screws 24. This enables self-holding pick-up of the bone screws 24 by means of the screw driver blades 26.

In FIG. 3 it can be clearly seen that the orifices 22 are constructed as through orifices in the plate 12. The thickness of the plate 12 is approximately 2.5 mm. This ratio guarantees that the plate 12 has no or only slight springing properties.

Figure 3A:
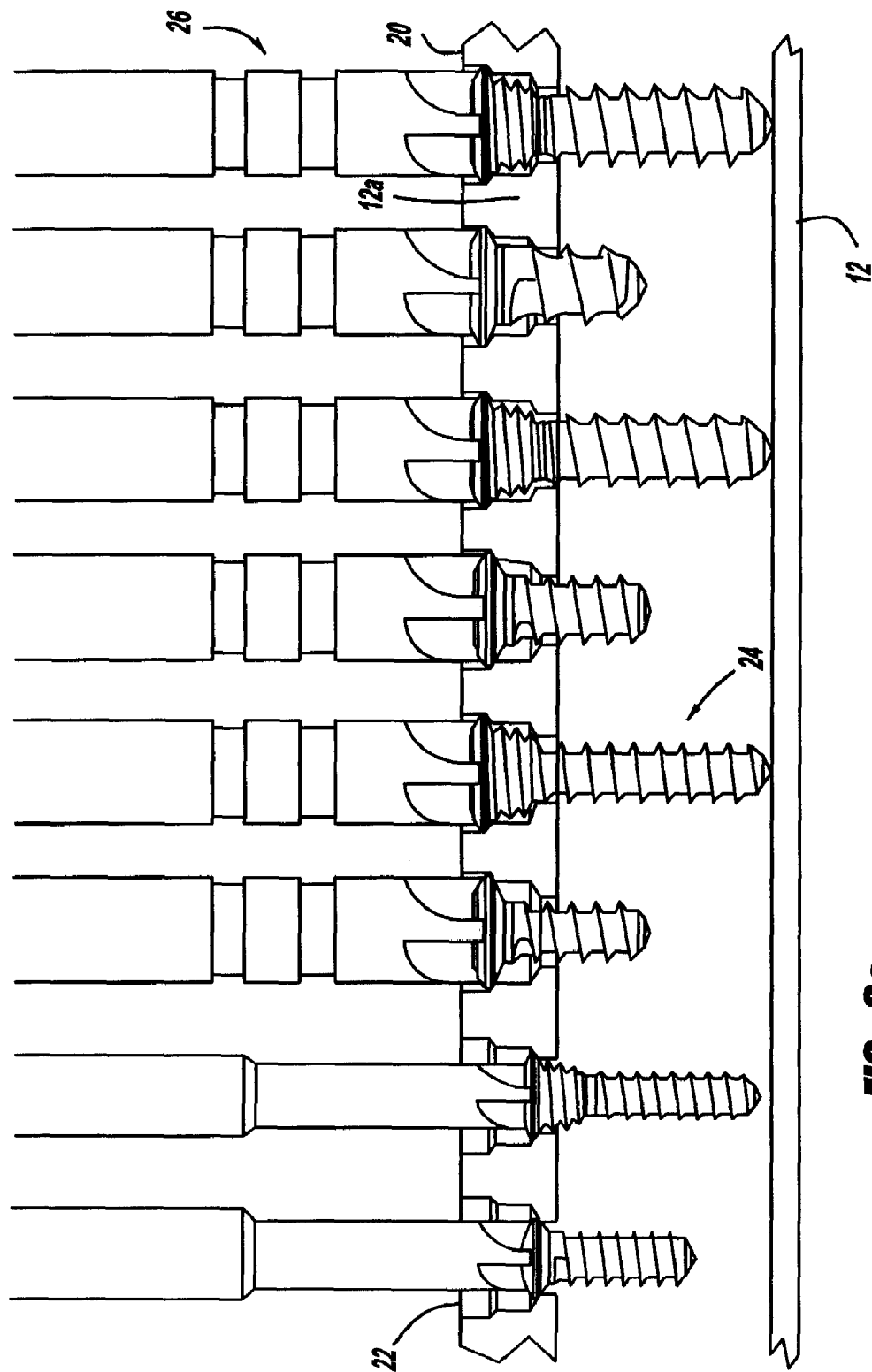
FIG. 3a shows a cross-section through an plate-shaped element of the keeping-ready device in FIG.3 in combination with a plurality of bone screws and removal instruments for the bone screws.

As can be seen from FIG. 3, the arrangement of the bone screws 24 as countersunk in relation to the surface 20 of the plate 12 has the advantage that the wall areas of the through orifices 22 above the heads of the bone screws 24 have a guiding function for the screw driver blades 26 when the screw driver blades 26 are inserted into the orifices 22 for the purpose of removing the bone screws 24. This guiding function is still reliably fulfilled if the diameter of the pick-up end of one of the screw driver blades 26 is considerably smaller than the maximum diameter of the through orifice 22. In the case illustrated in FIG. 3 this is due in particular to the fact that the orifice cross-section of the wall of the through orifice 22 is reduced in steps and therefore has a centering function in the direction of the head of the bone screw to be picked up for the two left screw driver blades in FIG. 3 with the smaller dimensioned pick-up end. As can be seen from FIG. 3a, an alternative version of the keeping-ready device 10 is shown, wherein first and second plate 12, 12a respectively, are shown. In this view, the first plate 12 is parallel to the second plates 12a. The second plate 12a is preferably distanced from the first plate 12 to such an extent that the bone screws 24 are kept ready by the keeping-ready device 10, e.q with their heads or tips lying on the second plate 12a.

FIG. 4 shows a detail enlargement of FIG. 3, wherein for the sake of clarity not all the bone screws and screw driver blades have been illustrated.

It can be seen from FIG. 4 that the delimitation walls of the through orifices 22 below the surface 20 of the plate 12 have in each case a reduction in inner diameter. More precisely, the inner diameter decreases in each case in three steps. The inner diameter of the through orifices 22 is largest immediately below the surface 20. A first cylindrical wall area with the largest diameter runs into a second cylindrical area of slightly smaller diameter. This second cylindrical area runs into a third cylindrical area with a smaller diameter than the second cylindrical area. The third cylindrical area borders on an underside 28 of the plate 12.

At the transition from the first to the second cylindrical area the wall of the through orifice 22 has a step in the form of a first circular-ring-shaped stop 30 and at the transition from the second cylindrical area to the third cylindrical area a further step in the form of a second circular-ring-shaped stop 32.

The step-shaped decrease in the inner diameter of the walls of the through orifices 22 illustrated in FIG. 4 allows secure picking up of bone screws with different head diameters. As a function of the head diameter of the bone screw to be picked up, when it is inserted into the through orifice 22 it comes into contact either with the upper stop 30 in FIG. 4, or with the lower stop 32 in FIG. 4. If one looks at FIG. 3, it can be clearly seen that the two left bone screws in FIG. 3 with their heads have come into contact with the lower stop (reference numeral 32 in FIG. 4) and the remaining bone screws with their heads into contact with the upper stop in FIG. 3 (reference numeral 30 in FIG. 4).

Figure 5:
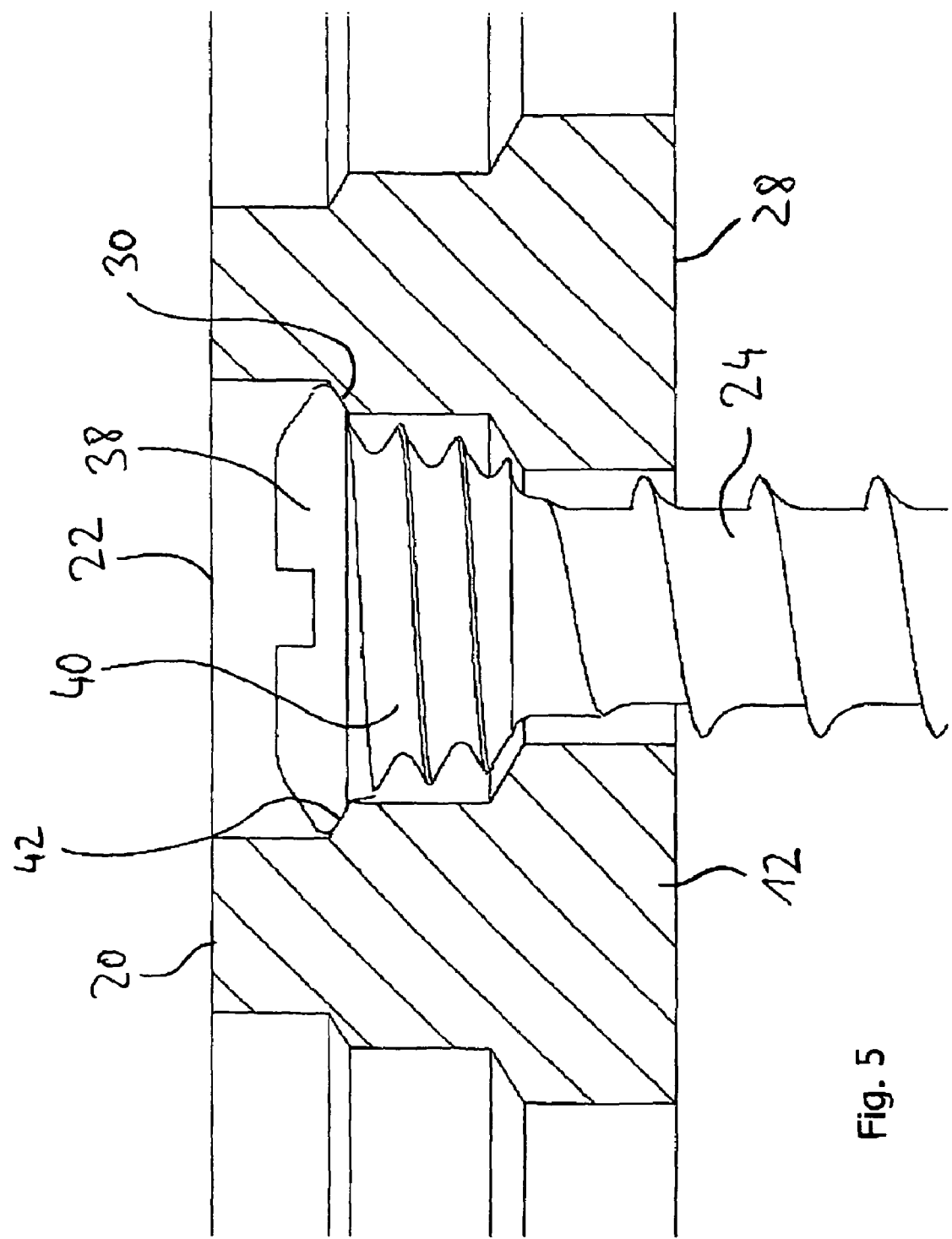
FIG. 5 shows an enlarged view of FIG. 4.

FIG. 5 shows a detail enlargement from FIG. 4 in the area of the left bone screw 24 in FIG. 4. For the sake of clarity, in FIG. 5 the right bone screw in FIG. 4 and also the screw driver blades 26 have been left out.

As can be seen from FIG. 5, the bone screw 24 has a screw head 38 with a head thread 40. The screw head 38 is provided on its radially outer end with a bezel 42, which cooperates in positive locking with the upper stop 30, running crosswise in relation to the surface 20 of the plate 12. The cooperation of the bezel 42 of the head 38 of the bone screw 24 with the conically constructed upper stop 30 effects self-centring of an inserted bone screw 24.

The above-described embodiment of the invention is intended to be an example of the present invention, and alterations and modifications may be effected thereto, by those of ordinary skilled in the art, without departing from the scope of the invention which is defined by the claims appended hereto.

The invention claimed is:

1. A system for keeping ready bone screws, comprising:
   a plurality of bone screws;
   a keeping-ready device for the bone screws, wherein the keeping-ready device includes a first plate with a plurality of orifices for inserting the bone screws and the keeping-ready device allows inserted bone screws to be kept ready countersunk in relation to the surface; and
   a removal instrument for removing a kept-ready bone screw from the keeping-ready device, wherein the removal instrument is dimensioned such that it is insertable into one of the orifices for removal of a kept-ready bone screw;
   wherein the orifices are arranged in the surface in a plurality of rows;
   wherein the keeping ready device includes a second plate which is distanced from the first plate to such an extent that the bone screws are kept ready lying on the second plate.

2. The system for keeping ready bone screws according to claim 1, wherein the removal instrument and the orifices are dimensioned such that delimitation walls of the orifices allow at least partial guiding of an insertion movement of the removal instrument.

3. A keeping-ready device for bone screws, comprising:
   a plurality of bone screws; and
   a surface in which a plurality of orifices for inserting the bone screws is provided, wherein the keeping-ready device allows inserted bone screws to be kept ready countersunk in relation to the surface;
   the surface including a first plate having a plate area in which the orifices are provided in a plurality of rows;
   wherein the first plate has a plate thickness wherein the ratio of area to thickness is chosen such that the first plate has no or only slight springing properties;
   wherein the surface includes a second plate which is distanced from the first plate to such an extent that the bone screws are kept ready lying on the second plate.

4. The keeping-ready device according to claim 3, wherein the orifices have delimitation walls which act as a guide for a removal instrument for the bone screws that is to be inserted into one of the orifices.

5. The keeping-ready device according to claim 3, wherein the orifices are configured as pocket holes.

6. The keeping-ready device according to claim 5, wherein the pocket holes are constructed in such a way that the bone screws are kept ready lying on the bottom of the pocket holes.

7. The keeping-ready device according to claim 3 or 4, wherein the delimitation walls of the orifices in a region below the surface have a reduction in inner diameter.

8. The keeping-ready device according to claim 7, wherein the reduction in inner diameter has an inner diameter at least partially gradually decreasing from the surface.

9. The keeping-ready device according to claim 8, wherein the inner diameter decreases continuously or in steps from the surface.

10. The keeping-ready device according to claim 7, wherein the reduction in inner diameter acts as a stop for a head of a bone screw to be kept ready.

11. A device for keeping bone screws ready, the bone screws having bone screw heads and the device comprising:
    a plurality of bone screws; and
    a surface in which orifices are provided for loosely keeping-ready the bone screws with countersunk bone screw heads in relation to the surface, the orifices having walls that act as a guide for a removal instrument for the bone screws when the removal instrument is inserted into one of the orifices;
    the surface including a first plate having a plate area in which the orifices are provided in a plurality of rows;
    wherein the first plate has a plate thickness wherein the ratio of area to thickness is chosen such that the plate has no or only slight springing properties;
    wherein the surface includes a second plate which is distanced from the first plate to such an extent that the bone screws are kept ready lying on the second plate.

12. The device according to claim 11, wherein the orifices include portions of reduced inner diameter that act as stops for the bone screw heads.

13. A device for keeping bone screws ready, the bone screws having bone screw heads and the device comprising:
    a plurality of bone screws; and
    a surface including a first plate in which a plurality of orifices for inserting the bone screws is provided, wherein the orifices have portions of a reduced inner diameter for cooperating with bone screw heads and wherein the portions of reduced inner diameter are placed such that the bone screw heads are kept ready countersunk in relation to the surface;
    wherein the orifices are arranged in the surface in a plurality of rows;
    wherein the surface has a thickness wherein the ratio of area to thickness is chosen such that the surface has no or only slight springing properties;
    wherein the surface includes a second plate which is distanced from the first plate to such an extent that the bone screws are kept ready lying on the second plate.

14. The device according to claim 13, wherein the orifices include portions of a widened inner diameter preceding the portions of reduced inner diameter in an insertion direction and wherein the portions of widened diameter constitute a guide for a removal instrument that is to be inserted into the orifices for removing the bone screws.

* * * * *

UNITED STATES PATENT AND TRADEMARK OFFICE
CERTIFICATE OF CORRECTION

| | | |
|---|---|---|
| PATENT NO. | : 7,350,643 B2 | Page 1 of 1 |
| APPLICATION NO. | : 10/758908 | |
| DATED | : April 1, 2008 | |
| INVENTOR(S) | : Capanni et al. | |

It is certified that error appears in the above-identified patent and that said Letters Patent is hereby corrected as shown below:

Title Page;
Page 1, Section 30, Foreign Application Priority Data; Please add --German Patent Application No. 103 01 690.2, filed on January 17, 2003--

Signed and Sealed this

Nineteenth Day of August, 2008

JON W. DUDAS
*Director of the United States Patent and Trademark Office*